(12) United States Patent
Blazer-Yost et al.

(10) Patent No.: US 11,701,358 B2
(45) Date of Patent: Jul. 18, 2023

(54) METHODS OF INHIBITING SERUM GLUCOCORTICOID INDUCED KINASE 1 (SGKI) AS A TREATMENT FOR SALT AND WATER BALANCE DISEASES

(71) Applicants: Indiana University Research and Technology Corporation, Indianapolis, IN (US); Universita Magna Graecia (UMG) at Catanzaro, Catanzaro (IT); Lead Discovery Siena, Siena SI (IT)

(72) Inventors: Bonnie L. Blazer-Yost, Indianapolis, IN (US); Nicola Perrotti, Catanzaro (IT); Silvia Schenone, Castelnuovo Berardenga (IT)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/487,239

(22) PCT Filed: Feb. 14, 2018

(86) PCT No.: PCT/US2018/018177
§ 371 (c)(1),
(2) Date: Aug. 20, 2019

(87) PCT Pub. No.: WO2018/156401
PCT Pub. Date: Aug. 30, 2018

(65) Prior Publication Data
US 2019/0365765 A1 Dec. 5, 2019

Related U.S. Application Data

(60) Provisional application No. 62/463,157, filed on Feb. 24, 2017.

(51) Int. Cl.
| | | |
|---|---|---|
| A61K 31/519 | (2006.01) | |
| A61K 9/00 | (2006.01) | |
| A61K 31/11 | (2006.01) | |
| A61K 31/145 | (2006.01) | |
| A61K 31/4439 | (2006.01) | |
| A61K 31/4709 | (2006.01) | |
| A61K 31/4965 | (2006.01) | |
| A61K 31/5377 | (2006.01) | |
| A61K 31/55 | (2006.01) | |
| A61K 31/585 | (2006.01) | |

(52) U.S. Cl.
CPC .......... *A61K 31/519* (2013.01); *A61K 9/0053* (2013.01); *A61K 31/11* (2013.01); *A61K 31/145* (2013.01); *A61K 31/4439* (2013.01); *A61K 31/4709* (2013.01); *A61K 31/4965* (2013.01); *A61K 31/5377* (2013.01); *A61K 31/55* (2013.01); *A61K 31/585* (2013.01)

(58) Field of Classification Search
CPC ...... A61K 31/519; A61K 33/24; A61K 45/06; A61K 9/0053; A61K 31/11; A61K 31/145; A61K 31/4439; A61K 31/4709; A61K 31/4965; A61K 31/5377; A61K 31/55; A61K 31/585; A61P 7/10; A61P 9/12
See application file for complete search history.

(56) References Cited

U.S. PATENT DOCUMENTS

| | | | |
|---|---|---|---|
| 2007/0191326 A1 | 8/2007 | Lang | |
| 2011/0130400 A1 | 6/2011 | Bury et al. | |
| 2014/0357640 A1* | 12/2014 | Nazare | A61P 19/00 |
| | | | 514/249 |
| 2015/0290206 A1 | 10/2015 | Gattone et al. | |

FOREIGN PATENT DOCUMENTS

| | | |
|---|---|---|
| WO | 2009111680 A1 | 9/2009 |
| WO | 2009146177 A1 | 12/2009 |
| WO | 2009146182 A1 | 12/2009 |
| WO | 2010011912 A1 | 1/2010 |
| WO | 2010011914 A1 | 1/2010 |
| WO | 2011119701 A1 | 9/2011 |
| WO | 2015048531 A8 | 4/2015 |

OTHER PUBLICATIONS

Nagy et al., Arch Psychiatr Nervenkr (1970). Apr. 12, 1979;226(4):319-24. (Year: 1979).*
Ahmed, Graduate School, Thesis, Dec. 26, 2015. (Year: 2015).*
Nakano et al., Hypertension Research (2013) 36, 277-284 published online Oct. 25, 2012, (Year: 2012).*
Price et al., Arch Neurol. 1976;33(1):15-20. (Year: 1976).*
Nagra et al. Cerebrospinal Fluid Research, vol. 7, Article No. 4 (2010). (Year: 2010).*
D'Antona et al., SI113, a Specific Inhibitor of the Sgk1 Kinase Activity that Counteracts Cancer Cell Proliferation Cellular Physiology and Biochemistry; 13-pages.
Ackermann et al., "EMD638683, a Novel SGK Inhibitor wiht Antihypertensive Potency", Cellular Physiology and Biochemistry, vol. 28, No. 1, Jan. 1, 2011, pp. 137-146.
Lang, et al., "Therapeutic Potential of Serum and Glucocorticoid Inducible Kinase Inhibition," Expert Opinion on Investigational Drugs, vol. 22, No. 6, Mar. 19, 2013, pp. 701-714.

(Continued)

*Primary Examiner* — Jean P Cornet
(74) *Attorney, Agent, or Firm* — Stinson LLP

(57) ABSTRACT

Methods of using serum glucocorticoid induced kinase 1 (SGK1) inhibitors for reducing the development of diseases related to salt and water balance, and in particular, hydrocephalus and/or hypertension, are disclosed herein. Particularly, the present disclosure is directed to the use of SGK1 inhibitors to inhibit transepithelial ion transport, such as in one embodiment, in the choroid plexus of a subject, thereby reducing cerebrospinal fluid (CSF) production or, alternatively, in another embodiment, to inhibit transepithelial sodium transport in the kidney collecting duct thereby reducing sodium reabsorption into the blood.

9 Claims, 4 Drawing Sheets

(56) References Cited

OTHER PUBLICATIONS

Lou et al., "Serum and Glucocorticoid Regulated Kinase 1 in Sodium Homeostasis," International Journal of Molecular Sciences, vol. 17, No. 8, Aug. 10, 2016, p. 1307.

Wang et al., "Up-regulation of Serum-and Glucocorticoid-induced Protein Kinase 1 in the Brain Tissue of Human and Experimental Epilespsy," Neurochemistry International, vol. 57, No. 8 Dec. 1, 2010, pp. 899-905.

* cited by examiner

METHODS OF INHIBITING SERUM GLUCOCORTICOID INDUCED KINASE 1 (SGK1) AS A TREATMENT FOR SALT AND WATER BALANCE DISEASES

CROSS REFERENCE TO RELATED APPLICATIONS

This application is a national phase application based on International Application Serial No. PCT/US 2018/018177 (WO 2018/156401), filed Feb. 14, 2018, which claims the benefit to U.S. Provisional Patent Application No. 62/463, 157, filed on Feb. 24, 2017, both of which are hereby incorporated by reference in their entireties.

BACKGROUND OF THE DISCLOSURE

The present disclosure relates generally to inhibition of serum glucocorticoid induced kinase 1 (SGK1) for treating diseases related to salt and water balance. Particularly, in one suitable embodiment, the present disclosure is directed to the use of 2-({1-(2-phenylethenyl)-4-[(2-phenylethy) amino]-1H-pyrazolo[3,4-d]pyrimidin-6-yl}amino)ethanol (SI 113), primarily known as a chemotherapeutic agent, for reducing the development of hydrocephalus. In another suitable embodiment, the present disclosure is directed to the use of SI 113 for reducing the development of hypertension.

SGK1 is an intracellular enzyme that is an important component of intracellular signaling pathways. Many of these pathways culminate in the activation of specific ion channels. The ion channels transport specific electrolytes from one fluid compartment to another. The movement of the electrolytes causes an osmotic movement of fluid. In some cases such as hydrocephalus and hypertension, the movement of electrolytes and fluid can cause, respectively, excess electrolytes and fluid in the brain, or excess electrolytes and fluid in the circulation.

Hydrocephalus can occur at any age and has multiple causes and is characterized by excess intracranial fluid. The disease may result in developmental delay, progressive neurological decline, blindness, or death, if untreated. Currently, surgery is the only effective long term treatment. Certain types of hydrocephalus may be treated with endoscopic procedures, including ventriculostomy (creating a bypass hole in the floor of the third ventricle) or irreversible coagulation of the choroid plexus, the intraventricular structures that produce the majority of cerebrospinal fluid (CSF). The most common surgical treatment is placing a CSF shunt—an implanted device that drains spinal fluid to another terminus of the body for reabsorption. All surgical procedures carry well-defined risks. Rare, but reported, complications for all surgeries include infection, neurologic deficit, and death. In addition to those risks, approximately 50% of shunts fail within 2 years and require surgical revision. In the U. S. alone, the cost of shunting is approximately $100 million dollars annually; half of this is for revision shunt surgery.

There are currently no durable, long term, effective medical treatments for hydrocephalus. Pharmaceutically reducing the production of CSF is a promising, novel treatment with the potential to revolutionize the treatment of this condition and spare patients the significant cost and morbidity related to surgery.

Additionally, hypertension is generally an age-related disease. After the age of 50, over 50% of adults have hypertension. It is known that excess reabsorption of the electrolyte, sodium, in the kidney collecting duct can increase the amount of fluid in the blood (blood volume) and, thereby increase blood pressure, causing hypertension. In a normal individual, blood pressure and the maintenance of normal blood sodium is controlled by hormones and other factors in the body to maintain fluid and electrolyte homeostasis. Certain drugs in clinical use for hypertension (mineralocorticoid receptor antagonists) block the binding of the hormones to their specific receptors and, thereby, decrease blood pressure. However, in many subjects, these drugs do not fully control the high blood pressure. SGK1 is an intracellular enzyme that mediates the aldosterone dependent activation of the sodium transporter in the kidney, thus contributing to maintenance of high blood pressure. The ability of specifically blocking this enzyme could provide an alternative or additive treatment for hypertension.

BRIEF DESCRIPTION OF THE DISCLOSURE

The present disclosure is generally related to reducing the development of diseases related to salt and water balance (e.g., hydrocephalus, hypertension). Particularly, it has been found that, in the brain, inhibition of serum glucocorticoid induced kinase 1 (SGK1) inhibits transepithelial ion transport stimulated by the activation of the transient receptor potential cation channel subfamily V member 4 (TRPV4), thereby inhibiting the production of cerebrospinal fluid (CSF).

Additionally, it has been found that inhibition of SGK1 in the kidney cells, which contain the epithelial sodium channel (ENaC), inhibits sodium transport in a reabsorptive direction which, in the body, would inhibit sodium and water movement from the kidney filtrate into the blood. In one embodiment, inhibition of SGK1 is obtained by the SGK1 inhibitor, SI 113.

Accordingly, in one aspect, the present disclosure is directed to a method for treating a salt and water balance disease in a subject in need thereof, the method comprising: administering an amount of a serum glucocorticoid induced kinase 1 (SGK1) inhibitor to the subject.

In another aspect, the present disclosure is directed to a method of reducing cerebrospinal fluid (CSF) production in a subject in need thereof, the method comprising: administering an amount of a serum glucocorticoid induced kinase 1 (SGK1) inhibitor to the subject.

In yet another aspect, the present disclosure is directed to a method of inhibiting transepithelial ion transport in a subject in need thereof, the method comprising: administering an amount of a serum glucocorticoid induced kinase 1 (SGK1) inhibitor to the subject.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

DETAILED DESCRIPTION

Figure 1:
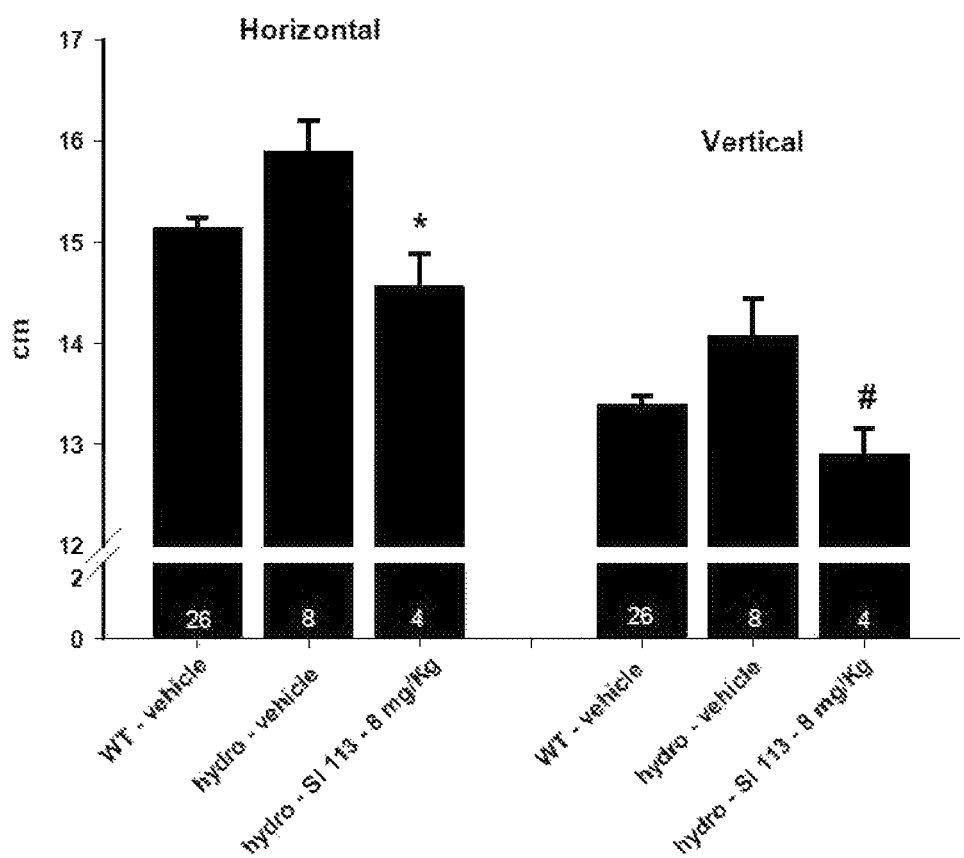
FIG. 1 depicts the effects of the SGK1 inhibitor, SI 113, on a hydrocephalic animal model as analyzed in Example 1.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As used herein, "reducing", "mitigating", "preventing" and "treating" are used interchangeably to refer to lessening the severity of and/or eliminating the symptoms of the disease, disorder, and/or condition.

Generally, the present disclosure is directed to the use of a serum glucocorticoid induced kinase 1 (SGK1) inhibitor for reducing a disease, disorder and/or condition resulting from salt and water imbalance (also referred to herein as a "salt and water balance related disease"). As used herein, the term "salt and water balance related disease" refers to a disease where there is an excess accumulation of an electrolyte or other osmotically active compound followed by an osmotic movement of water. Exemplary diseases, disorders, and/or conditions resulting from salt and water imbalance include hydrocephalus (e.g., congenital hydrocephalus, acquired hydrocephalus, communicating hydrocephalus, non-communicating hydrocephalus, hydrocephalus ex-vacuo, normal pressure hydrocephalus), hypertension, inflammatory responses (e.g., traumatic brain injury (TBI)), chronic edema and the like.

Particularly, it has been found herein that by inhibiting the activity of SGK1, transepithelial ion transport is inhibited. Particularly, inhibition of SGK1 has been found to inhibit transepithelial ion transport stimulated by the activation of the ion channel transient receptor potential cation channel subfamily V member 4 (TRPV4) in the choroid plexus of the brain.

Transient receptor potential cation channel subfamily V member 4 (TRPV4) is a member of the OSM9-like transient receptor potential channel (OTRPC) subfamily that in humans is encoded by the TRPV4 gene. TRPV4 protein is a $Ca^{2+}$-permeable, nonselective cation channel that is thought to be involved in the regulation of systemic osmotic pressure. TRPV4 also plays a crucial role in control of calcium-activated transepithelial ion flux, which is important for the production of cerebrospinal fluid (CSF) in the brain. Based on the foregoing, it has now been found that by inhibiting transepithelial ion transport stimulated by the activation of TRPV4 as with the use of a SGK1 inhibitor, the production of CSF is inhibited, further inhibiting the accumulation of excess fluid in the brain.

Additionally, it was found that administration of a SGK1 inhibitor inhibits transepithelial sodium transport in the kidney. By inhibiting the sodium transport, and particularly, inhibiting sodium reabsorption in the kidney, it is believed that the net result would be a lower concentration of sodium in the blood with a lower osmotic water movement, allowing for a lower blood pressure in the subject.

Suitable inhibitors of SGK1 include, for example, 2-({1-(2-phenylethenyl)-4-[(2-phenylethy)amino]-1H-pyrazolo[3,4-d]pyrimidin-6-yl}amino)ethanol (SI 113), having the chemical structure

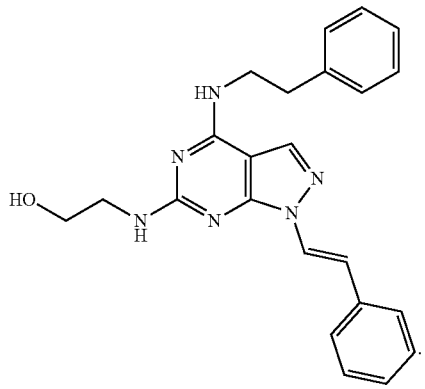 [SMILES: OCCNc1nc(NCCc2ccccc2)c2cnn(/C=C/c3ccccc3)c2n1]

Other suitable SGK1 inhibitors include 2-cyclopentyl-4-(5-phenyl-1H-pyrrolo[2,3-b]pyridin-3-yl)-benzoic acid (GSK 650394; GlaxoSmithKline) and N'-[2-(3,5-difluorophenyl)-2-hydroxyacetyl]-2-ethyl-4-hydroxy-3-methylbenzohydrazide (EMD638683; Merck).

GSK 650394

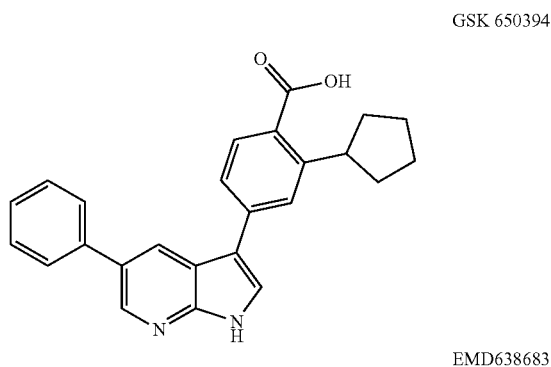

EMD638683

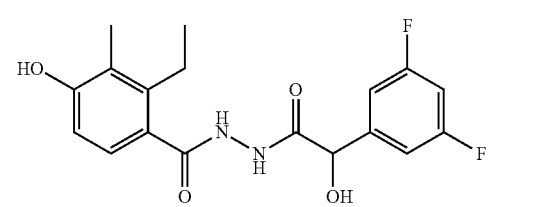

Suitable dosages of the SGK1 inhibitors for use in the methods of the present disclosure will depend upon a number of factors including, for example, age and weight of an individual, severity of salt and water balance disease, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

In one particularly suitable embodiment, the subject is administered from about 1 mg/Kg to about 10 mg/Kg, including from about 4 mg/Kg to about 8 mg/Kg.

The SGK1 inhibitors used in the methods of the disclosure can be administered as a pharmaceutical composition comprising the inhibitor (e.g., SI 113) of interest in combination with one or more pharmaceutically acceptable carriers. As used herein, the phrase "pharmaceutically acceptable" refers to those ligands, materials, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier", as used herein, refers to a pharmaceutically acceptable material, formulation or vehicle, such as a liquid or solid filler, diluent, excipient, solvent or encapsulating material, involved in carrying or transporting the active compound from one organ or portion of the body, to another organ or portion of the body. Each carrier must be "acceptable" in the sense of being compatible with the other components of the composition (e.g., synthetic compound) and not injurious to the subject. Lyophilized compositions, which may be reconstituted and administered, are also within the scope of the present disclosure.

Pharmaceutically acceptable carriers may be, for example, excipients, vehicles, diluents, and combinations thereof. For example, where the compositions are to be administered orally, they may be formulated as tablets, capsules, granules, powders, or syrups; or for parenteral administration, they may be formulated as injections (intramuscular, subcutaneous, intramedullary, intrathecal, intraventricular, intravenous, intravitreal), drop infusion preparations, or suppositories. For application by the ophthalmic mucous membrane route, they may be formulated as eye drops or eye ointments. These compositions can be prepared by conventional means, and, if desired, the active compound (i.e., SGK1 inhibitor) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the pharmaceutical compositions of the present disclosure can further include additional known therapeutic agents (e.g., ion channel blockers), drugs, modifications of the synthetic compounds into prodrugs, and the like for alleviating, mediating, preventing, and treating the diseases, disorders, and conditions described herein. For example, in one embodiment, the SGK1 inhibitors can be administered with one or more TRPV4 antagonists. As used herein "transient receptor potential vanilloid 4 antagonist" or "TRPV4 antagonist" refers to any compound capable of inhibiting or preventing the biological activities of a TRPV4 channel receptor. Suitable antagonists to TRPV4 channel receptors can be, for example, Ruthenium Red, RN-1734, RN-9893, capsazepine, citral, GSK205, HC-067047, GSK2193874, combinations thereof and the like. Further exemplary TRPV4 antagonists are described in US 2011/0130400; WO2009/111680, WO2009/146177, WO2009/146182, WO2010/011912, WO2010/011914, and/or WO2011/119701, each of which are incorporated by reference to the extent it is consistent herewith.

Suitable amounts of the TRPV4 antagonist can be, for example, from about 1 mg/Kg body weight to about 10 mg/Kg body weight.

In another embodiment, the SGK1 inhibitors can be administered with one or more known hypertension therapeutic agents. For example, the SGK1 inhibitors could potentiate the effects of other diuretics such as amiloride, furosemide or hydrochlothiazide. Moreover, since SGK1 is essential in transducing aldosterone dependent sodium retentive effects, SGK1 inhibitors could be considered in the treatment of secondary hyperaldosteronism as it occurs in cardiac failure, alone or in combination with mineralocorticoid receptor antagonists such as spironolactone and eplereonone.

When used in combination, it should be understood by one skilled in the art that, the SGK1 inhibitors can be administered concurrently with, prior to, or subsequent to, one or more other desired therapeutic agents (e.g., known hypertension therapeutic agents) or medical procedures. The particular combination of therapies (therapeutic agents or procedures) to employ in a combination regimen will take into account compatibility of the desired therapeutic agents and/or procedures and the desired therapeutic effect to be achieved. It will also be appreciated that the therapies employed may achieve a desired effect for the same disorder (for example, a compound described herein may be administered concurrently with another therapeutic agent used to treat the same disorder), or they may achieve different effects (e.g., control of any adverse effects).

The pharmaceutical compositions including the SGK1 inhibitors and, optionally, additional therapeutic agents and pharmaceutical carriers, used in the methods of the present disclosure can be administered to a subset of subjects in need of treatment for salt and water balance diseases, including hydrocephalus, hypertension, and the like. Some subjects that are in specific need of treatment for salt and water balance diseases may include subjects who are susceptible to, or at elevated risk of, experiencing salt and water balance diseases (e.g., hydrocephalus, hypertension, etc.), and the like. Subjects may be susceptible to, or at elevated risk of, experiencing salt and water balance diseases due to family history, age, environment, and/or lifestyle. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

Various functions and advantages of these and other embodiments of the present disclosure will be more fully understood from the examples shown below. The examples are intended to illustrate the benefits of the present disclosure, but do not exemplify the full scope of the disclosure.

EXAMPLE 1

In this Example, the effects of the SGK1 inhibitor, SI 113, in a hydrocephalic animal model were analyzed.

The effectiveness of SI 113 was tested in a genetic model of hydrocephalus, the Wpk rat model. In this model, the homozygous animals (TMEM67−/−) carry a single point mutation in TMEM67, one of a complex of proteins involved in the formation of the primary cilium. The homozygous affected animals have severe hydrocephalus and renal cystic disease. They typically survive for 18-21 days after birth, and the developing hydrocephalus can be monitored by measuring the head size in a manner analogous to measuring head sizes in human children.

In FIG. 1, the head sizes in both the horizontal and vertical dimensions are shown. Particularly, at post-natal day 15, hydrocephalic (hydro) animals treated with vehicle only had significantly larger head dimensions than the vehicle treated wild type (WT) animals. Treatment with SI 113 from post-natal day 7 to post-natal day 15 significantly decreased the head dimensions of the hydrocephalic animals (*p=0.009; # p=0.03, 1-tailed t-test). Further, after treatment with SI 113, the head dimensions of the hydrocephalic animals were not statistically different than the wild-type animals.

EXAMPLE 2

In this Example, the effects of SI 113 pretreatment on TRPV4 agonist stimulation in the PCP-R porcine choroid plexus cell line were analyzed.

Figure 2:
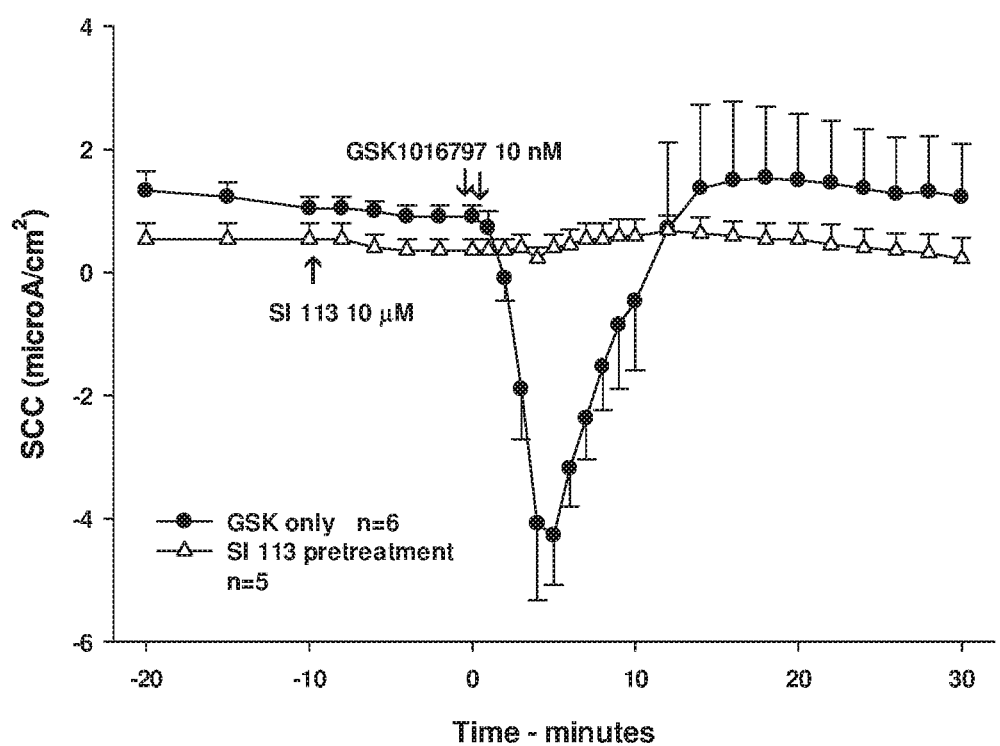
FIG. 2 depicts the effects of SI 113 pretreatment on TRPV4 agonist-stimulated ion transport across choroid plexus epithelial cells as analyzed in Example 2.

PCP-R (porcine choroid plexus, high resistance) cell line was grown to confluence on permeable Transwell supports. The PCP-R cell line is grown in tissue culture media consisting of Dulbecco's Minimal Essential media (DMEM) supplemented with 10% fetal bovine serum and penicillin (100 U/ml) and streptomycin (100 ng/ml). Cultured cells in both flasks and on Transwells had the media changed thrice weekly. After attaining a high resistance phenotype (days 10-12 after seeding on the Transwells), the cultures were removed from the plastic supports and mounted in an Ussing chamber for electrophysiological measurements (short-circuit current (SCC)) of net transepithelial ion transport. A negative deflection is indicative of anion absorption (CSF to blood) and/or cation secretion (blood to CSF). GSK1016797 is an agonist of TRPV4, an osmo- and mechano-sensitive channel which, when stimulated, allows $Ca^{2+}$ to enter the cells. The increased intracellular $Ca^{2+}$ secondarily stimulates $Ca^{2+}$-sensitive channels. In the case of the PCP-R cells, this process stimulates $Ca^{2+}$-sensitive $K^+$ channels causing the secretion of $K^+$ and, secondarily, water into the cerebrospinal fluid. As shown in FIG. 2, triangles indicate the cultures that were pre-treated with SI 113 at time t=−10 minutes. All cultures were stimulated with GSK1016797 at time t=0. Pretreatment of the cells with SI 113 completely blocked a subsequent response to GSK1016797.

EXAMPLE 3

In this Example, the effects of SI 113 on ENaC in a renal cell line were analyzed.

The mouse cortical collecting duct (mCCD) cell line is a continuous, high resistance cell line that has the characteristics of the principal cells that line the kidney distal tubules. In this segment of the tubules, a transport protein, the epithelial sodium channel (ENaC), is responsible for the reabsorption of sodium from the kidney filtrate and the return of this ion to the bloodstream. As the concentration of sodium increases in the blood, the increased osmotic concentration will cause a compensatory movement of water from cells all over the body into the blood and an increase in blood volume and blood pressure. ENaC is an important transport protein and its function plays a major role in the regulation of whole body salt and water balance. Increases in the activity of ENaC can cause hypertension and many hypertension medications target the intracellular signaling pathways that culminate in the activation of ENaC. For example, ENaC is inhibited by the diuretic, amiloride.

The mCCD cell line was grown in tissue culture media consisting of Dulbecco's Minimal Essential media (DMEM):Hams F12 supplemented with 5% fetal bovine serum and penicillin (100 U/ml) and streptomycin (100 ng/ml). Cultured cells in both flasks and on Transwells had the media changed thrice weekly. After seeding on Transwells, the cells were grown for 14-20 days to achieve a confluent, high resistance monolayer. The electrophysiological technique used to monitor transepithelial ion flux is identical to that used to obtain the data in FIG. 2. In the current Example, the basal activity of ENaC in the cells is the parameter that is monitored.

Figure 3:
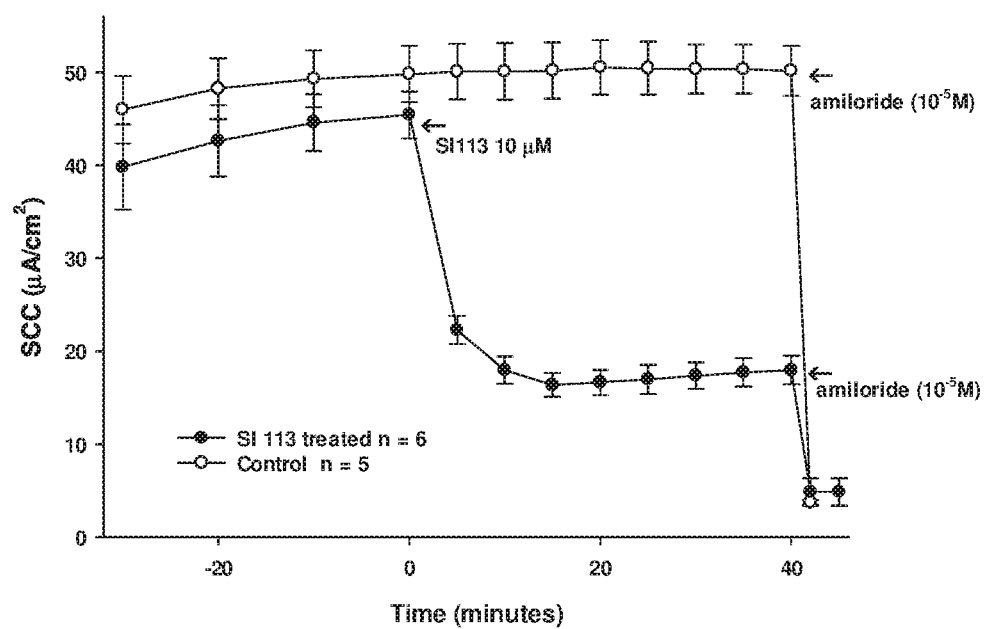
FIG. 3 depicts a series of electrophysiological experiments measuring net transepithelial ion transport across the mCCD cell line as analyzed in Example 3.

As can be seen in FIG. 3, when amiloride was added to the control cells (open circles), the short-circuit current (SCC) was strongly inhibited. This indicates that the SCC that is measured in the mCCD cells is due to sodium transport via ENaC. The sodium in this case was being absorbed (transported from the filtrate to the blood).

In the experimental samples (filled circles in FIG. 3), the addition of SI113 also caused a decrease in the SCC. Since the SCC is due to transepithelial sodium transport, this means that the S 1113 was inhibiting the sodium transport. In a body, this would mean that the SI 113 would inhibit sodium reabsorption in the kidney, and the net result would be a lower concentration of sodium in the blood with a lower osmotic water movement and, thus, a lower blood pressure.

EXAMPLE 4

In this Example, the effects of SI113 on hydrocephalus in the heterozygous Wpk rat model were analyzed.

Figure 4:
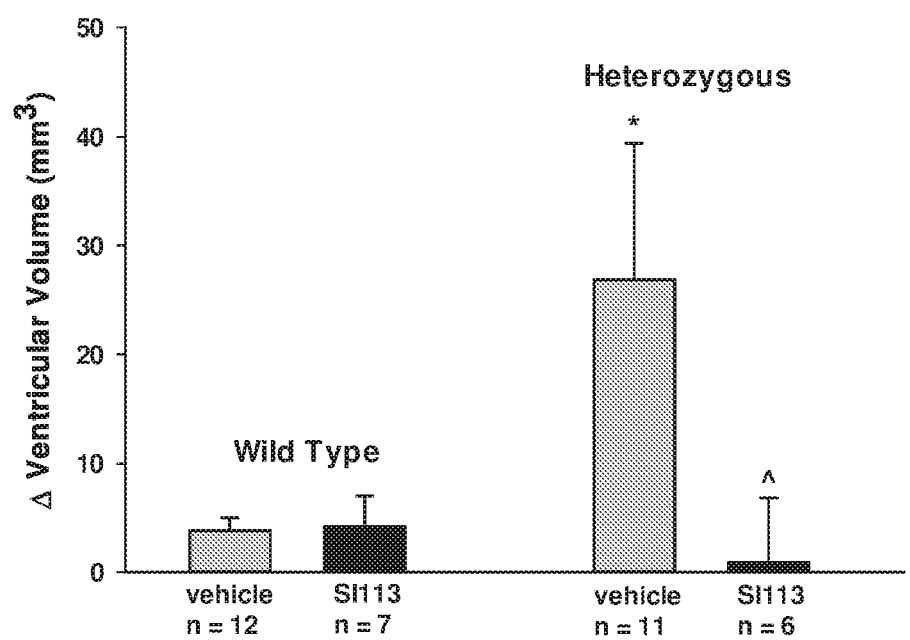
FIG. 4 depicts MRI quantification of the effects of SI113 on hydrocephalus in the heterozygous Wpk rat model. The bars represent the difference in volumes of the lateral ventricles measured at postnatal (P) day 7 and P15. The volumes were measured by MRI before treatment with vehicle or SI 113 (8 mg/kg BW; i.p. daily) and again after 8 days of treatment. The difference in the volume for each of the animals was calculated and the averages ±SEM are shown in the bar graph. The number of animals in each study is noted as n. Approximately equal numbers of male and female animals were used. Statistics were done with a Mann-Whitney test for nonparametric data. * indicates a statistically significant difference (P=0.015) between the wild-type and heterozygous vehicle-treated rats. ˆ indicates a statistically significant difference (P=0.039) between the vehicle- and SI113-treated heterozygous animals.

The Wpk rat model is unique in that the genetic defect causes a severe hydrocephalus in the homozygous affected animals (see FIG. 1) and a mild hydrocephalus in the heterozygous animals (see FIG. 4). The heterozygous animals live for at least year. These animals have no kidney disease but do have a mild form of hydrocephalus. In this model the hydrocephalus is not severe enough to change head dimensions so the effect of the SI113 on the hydrocephalus was measured using MRI. Specifically high resolution T2-weighted (T2W) MRI images were acquired using a 3T clinical MRI scanner (IMAGNETOM) outfitted with a dedicated 4 channel rat head coil and bed system. Images were acquired using a 3D SPACE sequence with the following acquisition parameters: (TA: 5.5 min; TR: 2080 ms; TE: 162 ms; FS: On; Ave: 2; Flip Angle: 150; Slice Thickness 0.2 mm: Matrix: 192×192; FOV: 35 mm×35 mm) yielding 0.18×0.18×0.2 mm resolution images. Volumes of interest on lateral ventricles were determined from threshold based image segmentation of native cerebrospinal fluid contrast, and images were quantified for lateral ventricular volumes using Analyze 12.0. The MRIs were conducted on each animal on day 7 and day 15 and the differences in lateral ventricular volumes were calculated (FIG. 4). As shown in FIGS. 1 and 4, treatment with SI113 effectively decreased the hydrocephalus whether measured by head dimensions in the homozygous, severe model of hydrocephalus (FIG. 1), or by MRI in the mildly hydrocephalic animals (FIG. 4).

What is claimed is:

1. A method to reduce a volume of cerebrospinal fluid (CSF) in a ventricular system of a brain in a mammal having communicating hydrocephalus, the method comprising:
   administering to the mammal a SI113, or a pharmaceutically-acceptable salt thereof;

inhibiting transepithelial ion transport from the choroid plexus to the ventricular system of the brain; and, reducing the volume of CSF in the ventricular system of the brain in the hydrocephalic mammal.

2. The method of claim 1, wherein the transepithelial ion transport is stimulated by activation of transient receptor potential cation channel subfamily V member 4 (TRPV4) channels in the choroid plexus.

3. The method of claim 1, wherein the transepithelial ion transport is transepithelial ion secretion.

4. The method of claim 1, wherein the subject is administered from about 1 mg/kg to about 10 mg/kg SI113.

5. The method of claim 1, wherein the subject is orally administered SI113.

6. The method of claim 1, further comprising administering a transient receptor potential cation channel subfamily V member 4 (TRPV4) antagonist in combination with the SGK1 inhibitor to the subject.

7. The method of claim 6 wherein the TRPV4 antagonist is selected from the group consisting of Ruthenium Red, RN-1734, RN-9893, capsazepine, citral, GSK205, HC-067047, GSK2193874, and combinations thereof.

8. The method of claim 1, wherein administering SI113 results in a normalization in volume of CSF in the ventricular system of the brain.

9. The method of claim 1, wherein the mammal does not have a kidney disease.

* * * * *